United States Patent [19]
Rhoades

[11] Patent Number: 4,713,535
[45] Date of Patent: Dec. 15, 1987

[54] OPTICAL KEYBOARD

[76] Inventor: Randy L. Rhoades, 1947 Delaware Ave., Swissvale, Pa. 15218

[21] Appl. No.: 772,553

[22] Filed: Sep. 4, 1985

[51] Int. Cl.$^4$ .................. H01J 40/14; G06F 15/40
[52] U.S. Cl. .............................. 250/221; 340/365 P
[58] Field of Search ............. 250/216, 221, 578, 234; 340/365 R, 365 P; 235/454, 460

[56] References Cited

U.S. PATENT DOCUMENTS

| | | | |
|---|---|---|---|
| 3,059,064 | 10/1962 | Lebell | 381/52 |
| 3,359,425 | 12/1967 | Smith | 250/222.1 |
| 3,478,220 | 11/1969 | Milroy | 250/221 |
| 3,665,164 | 5/1972 | Beveridge et al. | 235/460 |
| 3,673,579 | 6/1972 | Graven | 340/365 P X |
| 3,676,938 | 7/1972 | Thehub | 434/116 |
| 3,735,395 | 5/1973 | Iwabuchi et al. | 340/365 P |
| 3,761,877 | 9/1973 | Fernald | 250/220 R |
| 3,766,311 | 10/1973 | Boll | 358/94 |
| 3,818,448 | 6/1974 | Wilkins | 340/825.19 |
| 3,986,030 | 10/1976 | Teltscher | 250/349 |
| 4,081,623 | 3/1978 | Vogeley | 179/90 BD |
| 4,190,833 | 2/1980 | Bejting | 340/707 |
| 4,205,304 | 5/1980 | Moore | 340/365 P |
| 4,209,255 | 6/1980 | Heynau et al. | 356/152 |
| 4,238,792 | 12/1980 | Cohen et al. | 340/707 |
| 4,303,916 | 12/1981 | Hakaridani et al. | 340/712 |
| 4,405,197 | 7/1983 | Bejczy | 350/96.15 |
| 4,414,537 | 11/1983 | Grimes | 340/365 R |
| 4,480,183 | 10/1984 | Ely et al. | 250/227 |
| 4,534,668 | 8/1985 | Hildel et al. | 340/365 P X |
| 4,595,990 | 6/1986 | Garwin et al. | 340/365 P X |

OTHER PUBLICATIONS

"Application Prototype Board (APB) for MC6801/MC6803/MC68701 MCUs", by David Ruhberg, Motorola Application Note AN799A.

"Seeing is Writing with Eye Typer", by Mark Roth, Bill Levis/Post-Gazette (Pittsburgh), Oct. 15, 1984, Sansient Systems Technology.

"Non-Verbal Communications, Alternatives for the Handicapped", Prentke Romich Company, (Advertising Publication).

Primary Examiner—Eugene R. LaRoche
Assistant Examiner—David Mis
Attorney, Agent, or Firm—Buchanam, Ingersoll

[57] ABSTRACT

An optical keyboard includes a plurality of photosensors arranged in an X-Y coordinate system where a plurality of rows represent a plurality of X-axes and a plurality of columns represent a plurality of Y-axes. Each sensor represents input to data processing means. When a beam of light is cast onto a photosensor, the photosensor is actuated to transmit a coded signal to a microprocessor board. The microprocessor board scans the array of photosensors row by row sequentially to identify the column position of an actuated photosensor. The input received from the scanning operation is converted to data and transmitted through either a serial or parallel interface to a computer. Interface circuitry converts the data to a form readable by the computer. Thus, by selectively moving a light source to desired photosensors, specific information can be transmitted to a computer for printout or for operation of other devices remotely controlled by the computer to permit the computer to be operated by individuals unable to perform manual keyboard operations.

15 Claims, 10 Drawing Figures

OPTICAL KEYBOARD

BACKGROUND OF THE INVENTION

1. Field of the Invention

This invention relates to method and apparatus for the optical entry of data through an interface device to data processing equipment, and more particularly to an optical keyboard, which is interfaced with a computer to permit physically handicapped users to enter data into the computer.

2. Description of the Prior Art

It is well known in the art to utilize special purpose data input devices in place of the standard keyboard used to input data to electric typewriters and computers. The data input is supplied through an interface device that obviates the need to input data mechanically, in a conventional manner through a typewriter or a keyboard terminal of a computer. A wide spectrum of input devices are available for use by the physically handicapped, as in the case of individuals unable to execute the necessary hand movements needed for operating a mechanical keyboard. Interface devices are also available for those unable to verbalize data because of physiological handicaps, injury or other causes.

U.S. Pat. No. 3,059,064 discloses a data converter, by which visible information, such as a printed text, is converted to audible speech or photographs, to audio signals. This device has specific application for communication with non-sighted individuals, as well as, the illiterate. In this early development, a printed text is read and converted to audible speech. The output audible signals are in the form of speech quite similar to the audible speech provided by an individual reading the printed text outloud. In this manner, data imput, in the form of printed text, is converted to audio electrical signals representing speech.

More recently, as disclosed in the U.S. Pat. No. 3,761,877, light-emitting styluses, known as light pens, have been developed as an alternative to the conventional keyboard for supplying graphical data input to computers, displays, and other peripheral equipment. A graphic data tablet serves as a graphical interface between the input supplied by use of the light pen to a microprocessor. The light pen is moved by an operator over the flat writing surface of the graphic data tablet. The position of the light pen is detected by various means and associated circuitry converts the light pen position into digital or analog signals. The signals are a function of the position of the light pen on the tablet. The use of the light pen requires manual dexterity, and is not available to an operator who is physically or sight impaired.

U.S. Pat. Nos. 4,190,883 and 4,303,916 disclose apparatus for interfacing data processing equipment with an input terminal operable to receive input through a light pen. The disclosed light pen carries a light sensor, which develops a coded signal indicative of a specific selected item, when the item is illustrated with the light pen. When the light pen is placed upon a selected character of the input terminal, an optoelectric converter is supplied with light pulses representative of the selected character. In time coincidence with the light pulses, a digital code corresponding to the character appears on the output terminal. The code is transmitted to the RAM of the microprocessor and is capable of being reproduced as output in the form of alphanumeric text.

A wide variety of products are also available to provide nonverbal communication by the handicapped. These products enable an individual, not having the ability to verbally communicate, to transmit messages through various interface devices for converting input signals to output in either a printed or audio format.

U.S. Pat. No. 4,414,537 discloses a digital data entry glove interface device for use by the hearing impaired. A glove is equipped with sensors and associated electronic logic for use by one skilled in the use of a sign language. This permits a deaf or hearing impaired user wearing the data entry glove to input data to a receiving device by forming his or her hand into the character positions defined by the Signal Hand Manual Alphabet. Thus, a user who is hearing impaired and having no typing or other keyboard skills, can input information to a computer and communicate visually with others.

U.S. Pat. No. 3,818,448 discloses communication apparatus for non-verbal, handicapped persons who are unable to make use of sign language or other conventional communicating skills. A cabinet is provided with an array of indicator lamps and has acoustical devices, together with circuit means connectable with switches, which are operated by movement of some portion of the person's body to energize selected lamps, combinations thereof, or the acoustical devices. The switch means for controlling energization of the lamps can be actuated by left and right movement of the person's head. One switch may be used to select a particular row of indicators, while anothe switch is used to select a column.

U.S. Pat. No. 3,986,030 discloses an eye-motion operable keyboard, which includes a light source for directing a light ray at an eye of an operator. The light reflected from the eye of the operator actuates a selected light responsive sensor, arranged in a keyboard pattern on a panel. Each sensor has an output, which is connected to electrically actuated keys. The keys are positioned on a keyboard and are selectively actuated by the operator-reflected light striking one of the light responsive sensors. Preferably the light source is an infrared light source, and the sensors are responsive to rays of infrared light.

Not only are there known a wide variety of devices to permit handicapped individuals to utilize data processing equipment and other types of equipment of remote control by interaction with the human eye or light source, interface devices are also known for the sight operation of telephones. U.S. Pat. No. 4,081,623 discloses an optical interface for operating a telephone. This device also utilizes the "red-eye" effect of utilizing light reflected from the cornea of the eye to energize a sensor for transmitting electric signals to a logic circuit. Thus commands are transmitted to the logic circuit according to the number of times in sequence the eye is winked, or according to the length of time the eye is closed. A display unit displays digital information to the operator as it is sequenced through the digits available to the operator. The operator can stop the sequence at the appropriate digit by winking his eye. By selecting the proper sequence of digits, a telephone call can be placed.

Further examples of devices for the optical entry of data to data processing equipment, are disclosed in U.S. Pat. Nos. 4,205,304 and 3,478,220. Each of these devices utilize an optical device for actuating photosensitive devices positioned in a selected array. A series of light sources along a vertical axis of the array transmits a beam of light to corresponding photosensors on the opposite vertical side of a frame. The same arrangement is utilized to activate photosensors positioned along the horizontal axis of the array. The light sources actuate the photosensitive elements to emit output signals, which corresponds to an X-Y position in a coordinate system formed by the array of photosensitive devices. The output is then transmitted to a computer for carrying out a specific function corresponding to the input received.

U.S. Pat. No. 4,205,304 discloses a selection system circuit in which a signal corresponding to a selected position in a X-Y coordinate system is generated in response to the interruption of light transmission between a selected light emitter and light detector. A corresponding output signal is generated and is decoded for a selected control purpose; for example, enablement of a control mechanism.

While it is well known to transmit data and information to data processing equipment by other than manual keyboarding operations, for the benefit of both the physically handicapped and the nonverbal handicapped, the known devices are not readily adaptable to data processing equipment that is conventionally operated through a keyboard terminal. The known devices require substantial modification to the input terminal of the data processor to receive information in form not transmitted by a conventional keyboard. Because of the extensive modifications that are required to accommodate the known systems, each system must be customized to accommodate the optical entry of data. Overall, data entry equipment is not readily available for the physically handicapped. The equipment that is available is expensive, and not economically accessible to the handicapped to the extent to permit them to use the equipment to lead productive lives and pursue gainful employment. Therefore, there is need for interface apparatus to permit the optical entry of data through conventional data processing equipment.

SUMMARY OF THE INVENTION

In accordance with the present invention, there is provided interface apparatus for a data processor, that includes a data entry terminal, having an array of photosensors. The photosensors are positioned in a X-Y coordinate system, having a plurality of rows of photosensors parallel with a X-axis and a plurality of columns of photosensors parallel with a Y-axis. The photosensors are actuated between an active state and an inactive state, upon receipt of a source of energy to generate input signals. A microprocessor board is electrically connected in a first network to all of the photosensors aligned with the X-axis and in a second network to all of the photosensors aligned with the Y-axis. A data input terminal on the microprocessor board receives input signals from the actuated photosensors, representing a selected X and Y coordinate in the array of photosensors. Data processing means receives output signals from the microprocessor board in response to the input signals from the actuated photosensors, as instructions to perform a task. Means is provided for scanning the array of photosensors aligned with the X-axis sequentially row by row to identify the photosensors aligned with the Y-axis being actuated. The microprocessor board includes an output terminal connected to the data processing means for transmitting the output signals representing each actuated photosensor by a X and Y coordinate to the data processing means. The data processing means in response to the output signals from the microprocessor board is operable to perform a preselected task which corresponds to the actuation of the photosensors in a selected row and column when exposed to a source of light.

Further, in accordance with the present invention, there is provided an optical computer interface that includes an array of light sensitive elements positioned in an X-Y coordinate system. The coordinate system includes a plurality of the elements positioned in a first orientation and in a second orientation. The elements are each actuated when exposed to a light source to transmit a signal. Comparator means compares the signal received from each element with a reference signal and generates an output signal corresponding to actuation of the respective element. Scanning means sequentially inspects the first and second orientations of elements to identify in which one of the orientations an element is actuated and provide a coordinate for each actuated element. Further means is provided for converting the output signal representing a coordinate from the scanning means to a preselected signal for entry to a computer for data processing.

Further, in accordance with the present invention, there is provided a method for the optical entry of information for data processing, comprising the steps of actuating in sequence selected photosensors in a selected coordinate system array. Transmitted from the actuated photosensor is an output signal representative of the coordinate of the actuated photosensor. The output signals are sequentially scanned in the array of photosensors to identify the location of an actuated photosensor and provide a coordinate for each actuated photosensor. The output signals identified in terms of coordinates are converted to output signals having a format representative of information for input to data processing means.

Accordingly, the principal object of the present invention is to provide method and apparatus for supplying input data to a processor by actuating photosensitive elements in response to exposure to a light source, so as to permit one not being capable of performing manual data entry operations to supply input to a data processor.

Another object of the present invention is to provide interface apparatus linking an input terminal with a computer in a manner which facilitates a physically handicapped operator unable to operate a touch keyboard to enter data to a computer.

An additional object of the present invention is to provide a microprocessor for receiving input data upon actuation of photosensitive elements and supplying in response thereto coded output signals representative of the photosensitive elements and representing commands to a computer.

These and other objects of the present invention will be more completely disclosed and described in the following specification, the accompanying drawings, and the appended claims.

DESCRIPTION OF THE PREFERRED EMBODIMENTS

Figure 1:
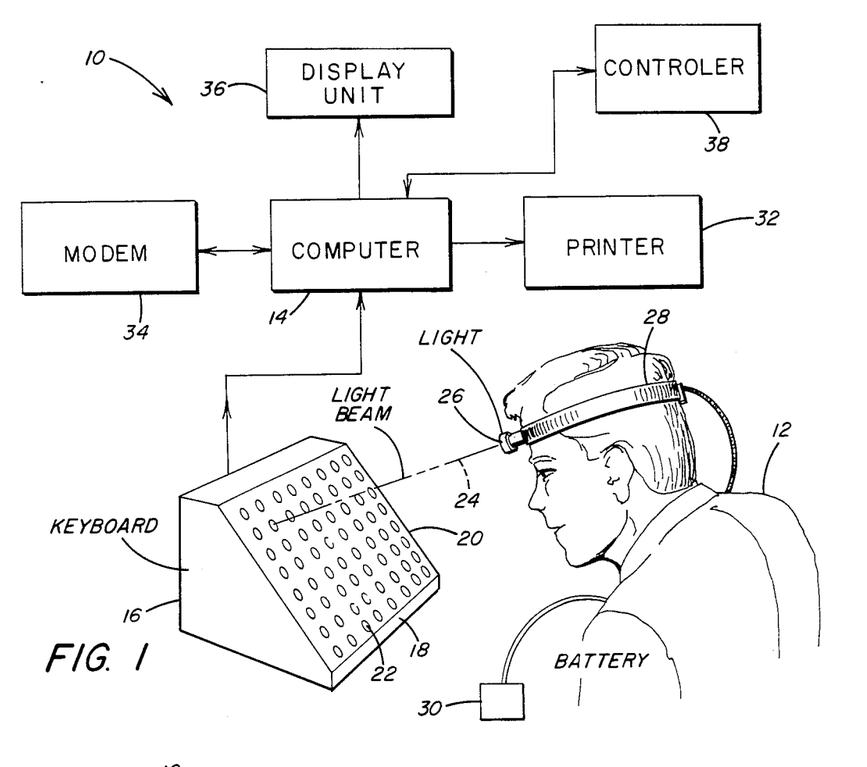
FIG. 1 is a schematic illustration of a system for optically supplying input to data processing equipment.
Figure 2:
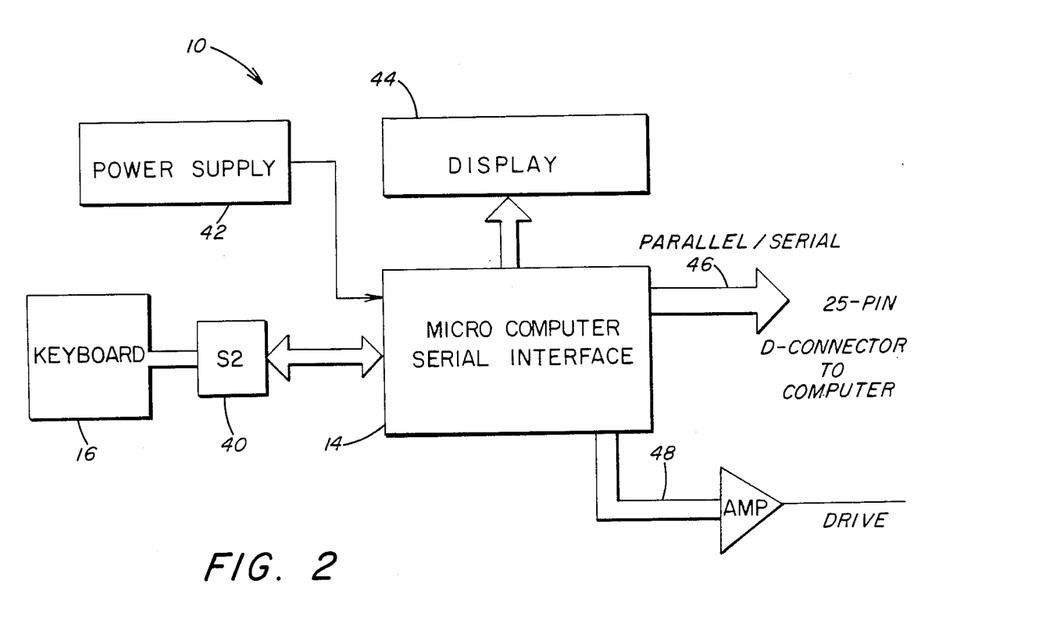
FIG. 2 is a block diagram, illustrating the components for interfacing the optical input of the data to the data processing equipment.

Referring to the drawings, and particularly to FIGS. 1 and 2, there is illustrated the components of optical data interface apparatus 10 for use particularly by a handicapped operator 12 to enter alphanumeric data for processing by a computer 14 or any other type of data processing equipment. The apparatus 10 is operable for use by the operator 12 without the need for the conventional entry of data through a manual keyboard, and consequently is particularly adaptable for a handicapped operator unable to perform manual keyboarding operations.

Figure 3:
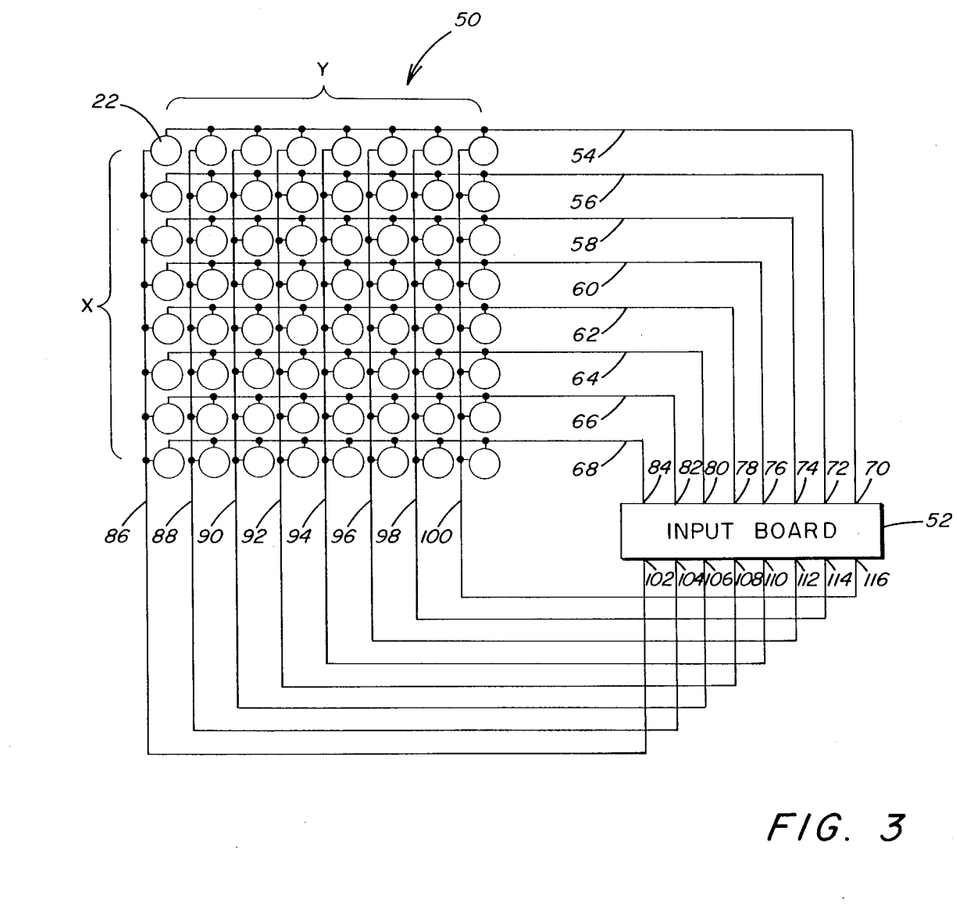
FIG. 3 is an electrical schematic of an optical keyboard for sensing light and transmitting data to the data processing equipment.

In accordance with the present invention, the computer 14 receives data entered by the operator 12 through an optical keyboard 16. The keyboard 16, as schematically shown in FIG. 1, includes a housing 18 having an apertured frame 20. A plurality of energy sensitive devices 22, such as photosensors illustrated in FIG. 3, are mounted in the housing 18 for display through the respective apertures of the frame 20. The photosensors 22 are shown positioned in a X-Y coordinate system where the sensors 22 are arranged in rows of sensors 22 aligned parallel with the X-axis and columns of sensors 22 aligned parallel with the Y-axis. However, it should be understood that the array of sensors 22 can be positioned in other geometric arrays, such as circular, triangular, and the like.

The sensors 22 are normally maintained in an inactive state and are activated by a source of light energy of a preselected magnitude. As illustrated in FIG. 1, the sensors 22 are selectively activated by directing a concentrated beam of light 24 from a source 26 which is secured, for example, to the head of the operator 12 by a headband 28. The source 26 is operable to cast a light beam 28 upon a selected one of the sensors 22 by head movement of the operator 12. The light beam 24 may be a visible beam of light or an infrared beam of light. The light beam 24 may be modulated to reduce ambient light interference.

Conventionally, the light source 26 is powered by a battery 30 electrically connected to the light source 26. A laser can also be utilized to reduce the spread of the beam over the distance between the light source 26 and the array of light sensors 22 on the frame 20.

Preferably, each photosensor 22 is associated with a light emitting diode (LED) which illuminates to indicate to the operator which sensor 22 in the array has been actuated, particularly for use with an infrared light source. After a preselected time of reception of the light beam 24 by the selected sensor 22, the sensor is activated to transmit through interface circuitry, illustrated in FIG. 4, a coded output signal to the computer 14. The signal received by the computer 14 from the interface circuitry corresponds to the sensor 22, having a preselected position in the coordinate system of the keyboard 16. Upon receipt of the coded signal, the computer 14 will process the data entry from the keyboard 16 and perform a corresponding task, again based upon the position of the activated sensor 22 in the array of sensors 22.

As desired, the computer 14 can be programmed to perform a wide variety of tasks in response to a succession of coded signals received from the keyboard 16 by selected actuation of the light sensors 22. In this manner, the computer 14 is operated to, in turn, operate selected peripheral devices. For example as illustrated in FIG. 1, the computer 14 is linked to operate a printer 32 to provide a record of the data entry through a word processing program. The computer 14 can also be linked to a modem 34, for telephone transmission of output data from the computer 14 through the optical keyboard 16. A digital display of the computer output can be viewed on a unit 36, as shown in FIG. 1, linked to the computer 14. In addition to performing conventional data entry and retrieval tasks through the optical keyboard 16, the keyboard 16 can be linked by the computer 14 to a controller 38, by which a wide variety of mechanical tasks can be performed in a remote control manner. This permits a handicapped person to operate a wide range of computer controlled equipment to perform tasks not otherwise capable of being performed by the handicapped.

Now referring to FIG. 2, there is diagrammatically illustrated the operating system for the optical data interface apparatus 10, which includes as one of the basic units the optical keyboard 16, discussed above and illustrated in FIG. 1. The keyboard 16 is operable to transmit input to the computer 14, as for example, a microcomputer, as well as receive input from the computer 14 for the purpose of scanning the array of light sensors 22. As illustrated by the flow chart in FIG. 6A after the conventional steps of initializing the devices and the memory, the keyboard 16 is scanned row by row in repeated succession to monitor actuation of the sensors 22 in the scanned row. The computer 14 identifies which row is being scanned, the X coordinate, and the column position of the sensor 22 in the row which is activated, the Y coordinate. The X, Y coordinate data is entered in the computer 14. If an actual sensor is detected, the row (X coordinate) and column (Y coordinate) are detected and converted to a usable code, such as ASCII. The scanning operation continues row by row.

In one embodiment, the keyboard can be connected to the computer through a serial interface board 14 as shown in FIG. 2. A typical serial interface connection would be accomplished by connecting the keyboard to a microcomputer through a connector, such as a 25 pin subminature D female connector, as known in the art. The keyboard 16 can also be connected to a computer through a standard RS-232 cable connection. Therefore, the computer is operable to both receive output from the keyboard and convert the output to usable form, as well as, scan the keyboard for actuation of the sensors 22.

The computer can be powered by either an external conventional source, such as a battery power supply 42 shown in FIG. 2, or the computer may itself supply the power for the operating system. In response to the signals received from the keyboard 16 upon actuation of the sensors 22, the computer decodes the signals to determine the operation to be performed as requested by the keyboard operator. The responsive action can be recorded on an alphanumeric display 44, shown in FIG. 2. In this manner data from the computer can be displayed for the operator of the keyboard 16, or the alphanumeric data on the display 44 can be transmitted to other individuals when the operator of the keyboard 16 is unable to speak.

The display 44 can include not only an alphanumeric readout, but a readout through a printer or a CRT. The output can also be expressed in the form of tones or an artificial voice. Thus the keyboard operator 12 is capable of transmitting data to and receiving data from the computer in a wide variety of formats.

The action taken by the computer is dependent upon the programming of the computer. Any software programming run by the computer using data input through a standard keyboard can be run using the optical keyboard 16 of the present invention.

The connection of the optical keyboard 16 to the computer can be accomplished in one mode by a seven wire parallel link, in which case the computer scans the array of sensors 22, using a three bit binary counter. The computer senses the column code returned to the output from the sensors 22. If a sensor 22 is activated, then a strobe signal in a three bit binary code corresponding to the column where the light beam was detected is sent to the computer. If a signal is not present, the strobe signal is not sent to the computer and no key is detected in the particular row scanned.

The operation of successively scanning the rows of sensors 22 along the x-axis in a X-Y coordinate system takes place many times each second. The computer scans the array along the rows and thereby identifies the particular column (y-axis) in which a sensor 22 is actuated for a particular row. In this manner, the specific input by the operator through a matrix is identified and converted to a coded signal representing the operation to be performed by the computer.

The computer can also be interfaced with the keyboard 16 through a nine or ten wire parallel mode. Again, data entry is delivered to the computer corresponding to the actuated sensor 22. A strobe signal is generated to indicate the presence of the code or key. The consequent code generated upon actuation of the sensor 22 can be a standard ASCII code. Thus, actuation of a sensor 22 transmits a selected code, which is placed on the data input lines to the computer. Correspondingly, the strobe signal fluctuates between a high and low threshold value upon receipt of the data input to the computer.

A standard serial RS-232 connection in a third mode links the keyboard 16 to the computer 14. In this manner, data can be transmitted at preselected rates, for example, 150, 300, 600, 1,200, 4,800, 9,600 etc. bits per second.

In one mode of operation, as illustrated in FIG. 1, with the light source 26 attached to a portion of the body of the operator, such as the operator's head, the operator selects which sensor 22 in the array will be actuated or the sequence in which the sensors 22 are illuminated, based on the computer controlled tasks to be performed. This is accomplished by the operator 12 moving his head to the desired position to direct the beam 24 of light upon the selected sensor 22. In response to the reception of light, the sensor 22 is actuated, and actuation of the sensor may be fed back to the operator 12 in the form of illumination, as by a light emitting diode.

Actuation of a sensor 22 generates a signal in coded form, which is transmitted to the computer to, actuate the computer to perform a specific function. The actions taken by the computer in response to the signals received from the keyboard 16 upon actuation of the sensors 22 is dependent upon the programming of the computer. In this manner, any computer or data processing operation that is performed by conventional keyboarding procedures can be performed by the interfacing of the optical keyboard 16 with the computer.

The output of the computer in response to the input from the optical keyboard 16 can be in a variety of forms. The output can be transmitted through a parallel or serial output 46. A standard 25 pin D-type connector can be utilized. The output can also be amplified for use in a drive mode for operation of remote control equipment or operation of a disk drive.

Now referring to FIG. 3, there is illustrated a matrix, generally designated by the numeral 50, of sensors 22 in a X-Y coordinate system. The sensors 22 may be selected from any known type of photosensor elements, which are responsive to either visible light or infrared light. The sensors 22, when exposed to a beam of light 24, as shown in FIG. 1, are switched between an inactive state and an active state whereby an electric signal is generated for transmission as input to the computer 14.

The sensors 22, in one mode of operation, can be switched from a normally inactive state to an active state upon reception of a beam of light. The sensors 22, in another mode of operation, can be switched from a normally active state to an inactive state.

The array of sensors 22, shown in FIG. 3, is positioned in the matrix 50 formed by parallel rows of sensors 22 aligned with the X-axis and parallel columns of sensors 22 aligned with the Y-axis. The matrix 50 is electrically connected to an input board or plug 52. A plurality of conductors 54–68 connect each of the rows of sensors aligned with the X-axis to pins 70–84 respectively of the plug 52. Similarly, each of the sensors 22 in their respective columns of the matrix 50 aligned with the Y-axis, are conducted by conductors 86–100, to pins 102–116 respectively of the plug 52. The plug 52 is in turn connected to a selector amplifier board, generally designated by the numeral 118 in FIG. 4.

Figure 4:
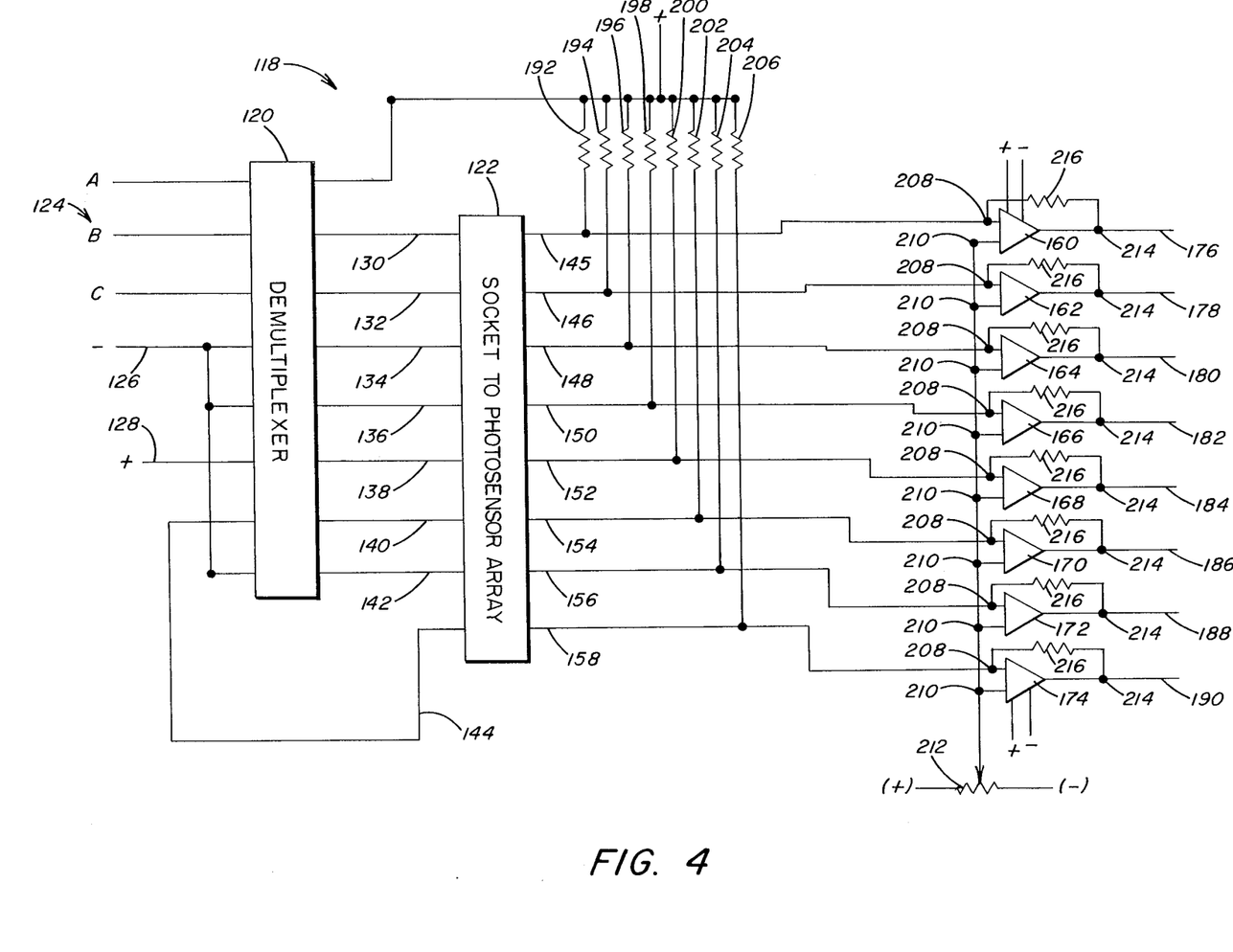
FIG. 4 is an electrical schematic of a selector amplifier board for interfacing the data input from the optical keyboard shown in FIG. 1 to the data processing equipment.

The selector amplifier board 118, as shown in FIG. 4, includes a selector device 120, such as, a demultiplexer. The selector device 120 includes an output terminal connected through a socket 122 to the plug 52 of the matrix 50 and an input terminal generally designated by the numeral 124. Conductors 126 and 128 connect the demultiplexer 120 to a power source. The socket 122 is connected through conductors 130-142 to the selector device 120 and through conductors 145-158 to amplifiers 160-174, respectively as shown in FIG. 4. The amplifiers 160-174 are connected by conductors 176-190 to the input terminal of the demultiplexer 220, shown in FIG. 5. With this arrangement the array 50 of sensors 22 transmits signals to, as well as, receives signals from the computer.

In a scanning operation, the computer 14 transmits pulses or signals through the socket 122 to the plug 52 associated with the sensor array 50. The selector device 120 selects data in the scanning operation performed by the computer to energize one of the respective rows of sensors 22. Signals are transmitted from the photosensor array 50 to socket 122 and through conductors 130-144 to the amplifiers 160-174 and the demultiplexer 220.

Through the input terminal 124 shown in FIG. 4, the selector device 120 transmits signals in the form of pulses through socket 122 to the plug 52 shown in FIG. 3. These pulses, in turn, are transmitted through pins 102-116 and conductors 86-100 respectively to the rows of sensors 22 in succession. Upon receipt of the signals by the sensors 22 in a row, all the sensors 22 of the row are activated so that in the scanning operation when a beam 24 of light is cast upon a sensor 22, the activated sensor transmits a signal representing a specific column in that row.

An actuated sensor 22 transmits a signal to the respective conductor 54-68. Each sensor 22 in each row (x-axis) is connected by a respective one of the conductors 54-68 to the plug 52. Accordingly, a signal is transmitted on one of the respective conductors 54-68 to one of the corresponding pins 70-84 of the plug 52. From the plug 52 a signal representative of the column designation (y-axis) for the actuated sensor 22 in the scanned row is transmitted to the socket 122, shown in FIG. 4.

The output signals from the sensors 22 are applied to the socket 122 (FIG. 4) and are transmitted through the conductors 145-158 to the amplifiers 160-174, respectively. The outputs from the amplifiers 160-174 are biased to the inactive state when the corresponding sensor is inactive by a bank of resistors 192-206, connected to the conductors 145-158 respectively.

As further illustrated in FIG. 4, the amplifiers 160-174 are arranged in a comparator network. Each amplifier includes an input terminal 208 for receiving input signals from the output terminals of the socket 122 in response to the keyboard sensors 22 which have been actuated by the light beam 24. Each amplifier 160-174 also includes a second input terminal 210 which is connected to a reference point 212. With this arrangement, the reference point 212 applies a reference voltage or bias point for each amplifier 160-174.

An output terminal 214 of each amplifier is connected in a feedback circuit through a resistor 216 to the amplifier input terminal 208 to establish a bias at the input of each amplifier. In the absence of a signal from the socket 122, each amplifier 160-174 normally generates a high level voltage at the output terminal 214. Thus a fixed voltage level is applied to each of the conductors 176-190, in the absence of an actuated photosensor 22.

When a photosensor 22 is actuated by the light beam 24, the voltage applied to the input terminal 208 of the respective amplifier exceeds the reference voltage applied to the input terminal 210. The amplifier generates an output signal which is more negative than the reference voltage at terminal 210. The input to the amplifier is representative of the analog signal received from the respective sensor 22. The output from the amplifier is a digital signal by which a command is entered in the computer. In the absence of an input signal at the amplifier terminal 208, the opposite digital state exists at the output terminal 214 of the amplifier.

FIG. 3 illustrates an 8×8 matrix of sensors 22 and is only one example. A 10×6 matrix or the like can be utilized. With the illustrated example the eight input signals are transmitted through the amplifiers 176-198 to an encoder, which will be explained later in greater detail, transmission to the computer for digital processing. With this arrangement where scanning signals are applied successively to each row (x-axis) of sensors 22 in the matrix 50, the determination of which sensor (y-axis) in the entire array has been actuated is limited to a scan of the sensors in the row being searched. Thus, a specific X-Y coordinate is identified by the computer upon actuation of any sensor 22 in the matrix 50. While the selector device 120 scans the matrix of sensors 22, the output signal generated by an actuated sensor 22 is converted from an analog signal to a digital signal for processing of the command requested by the operator.

With an 8×8 matrix of sensors 22, 64 individual codes are entered; however, only eight amplifiers are required to convert the 64 analog signals to corresponding digital signals. In this manner the number of amplifiers required for the digital conversion is substantially reduced. An individual amplifier is not required for each sensor, providing a simplified structure for analyzing the data entered by the optical keyboard 16.

Each of the above described amplifiers 160-174 functions as an operational amplifier to compare the signal coming from the photosensors 22 of the keyboard 16 with the value of the reference signal received from the voltage reference point 212. In the absence of a signal from the keyboard 16, the amplifiers 160-174 transmit through conductors 176-190 a high output signal. The reference voltage applied to each amplifier input terminal 210 to establish a bias point is adjustable by operation of the potentiometer 212.

The voltage applied to the amplifier input terminals 210 is adjustable to compensate for varying light conditions, under which the keyboard 16 is operated. In this manner, only those signals which exceed the threshold voltage for the amplifiers, are detected as signals exceeding the reference voltage at the output terminals 214.

The selector amplifier board 118, illustrated in FIG. 4, is operable for inputting data to a computer that utilizes a standard keyboard. With a standard keyboard, the data is transmitted to the computer to perform specific functions in accordance with the programmed operation of the computer. Therefore rather than use a standard keyboard, the optical keyboard 16 in accordance with the present invention is operable to transmit the instructions in coded form to the computer. In view of the operation of scanning the sensors 22, the computer must be programmed to receive input from the sensors 22.

Figure 5:
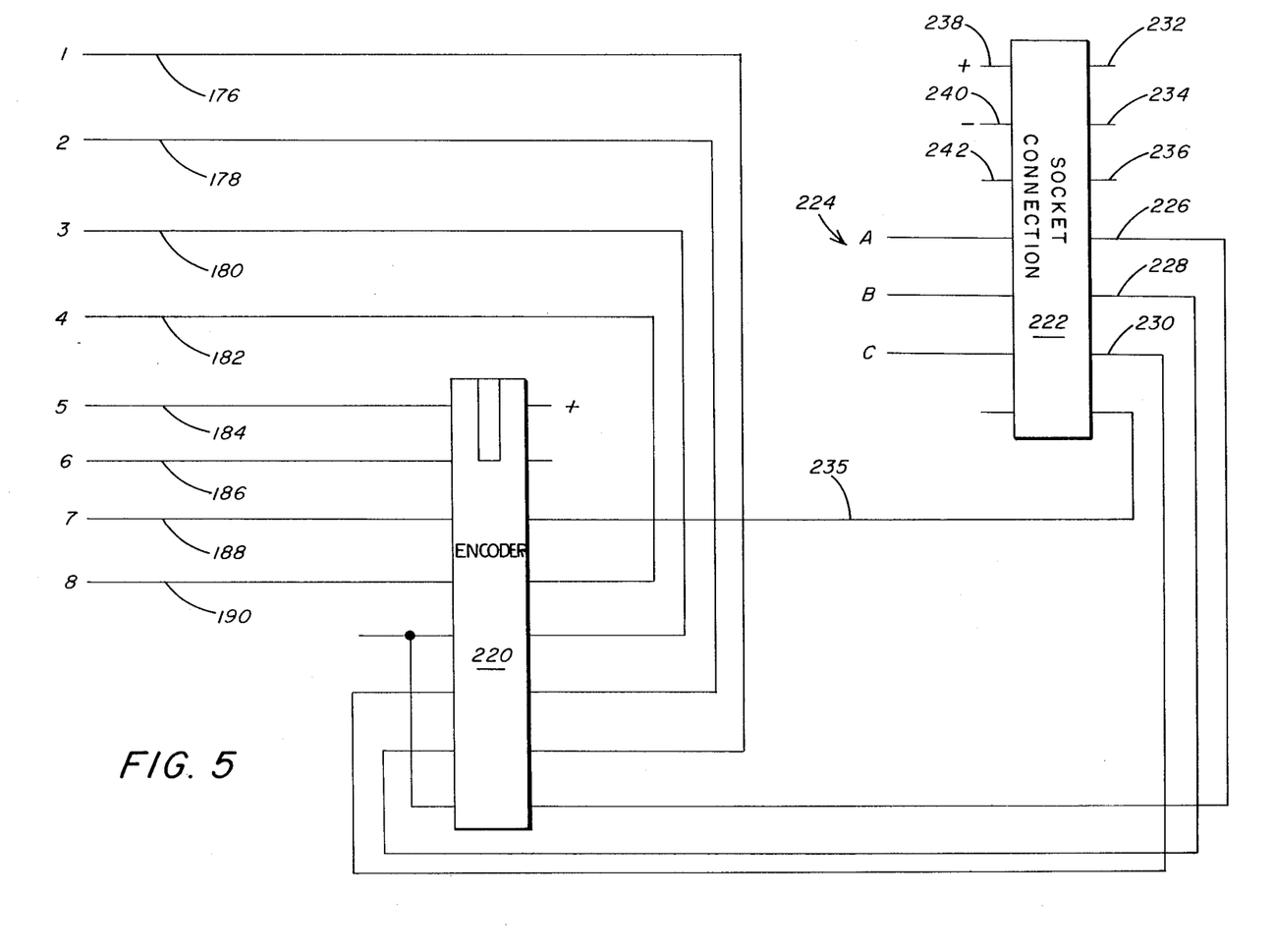
FIG. 5 is an electrical schematic similar to FIG. 4 illustrating further details of the selector amplifier board for interfacing the optical keyboard to data processing equipment.
Figure 6:
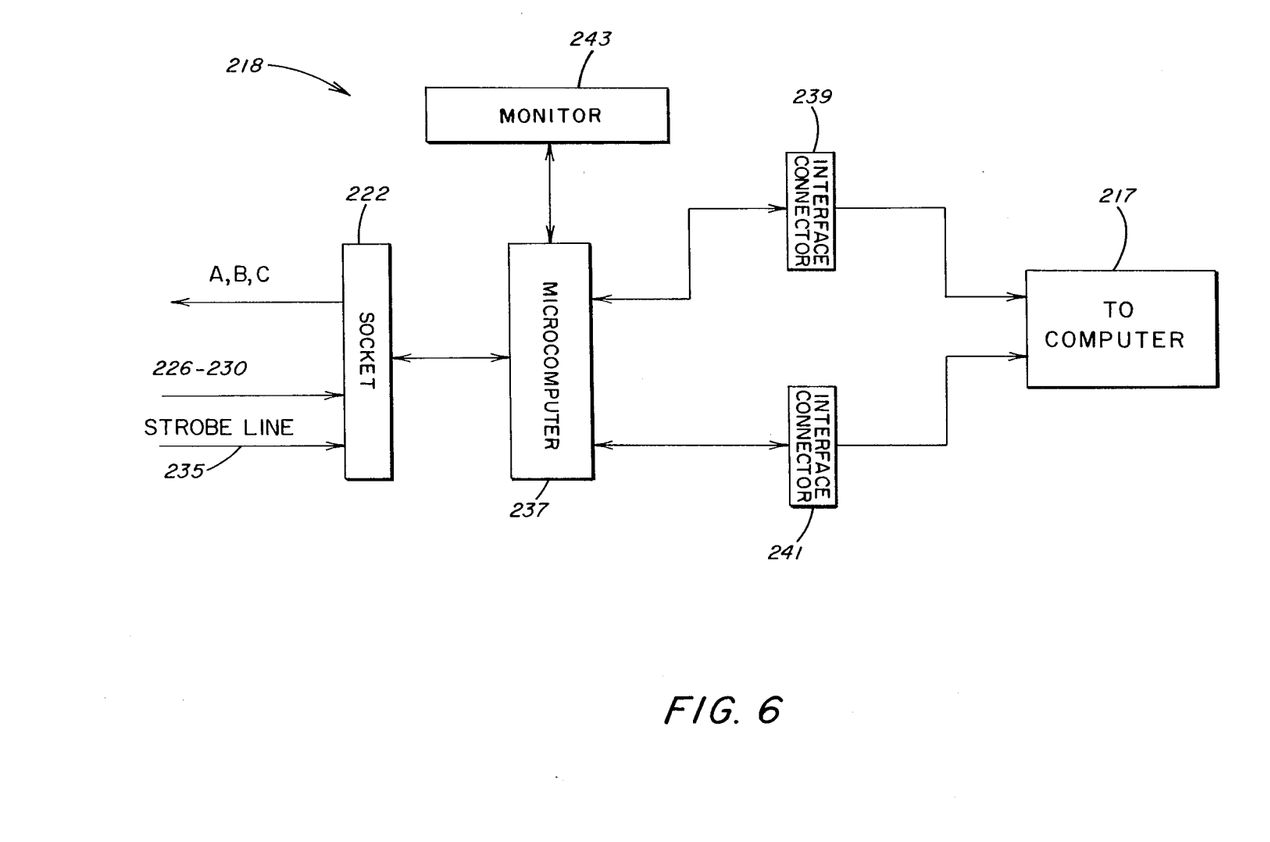
FIG. 6 is a block diagram of the connection between the selector amplifier board of FIG. 5 and the data processing equipment.
Figure 6A:
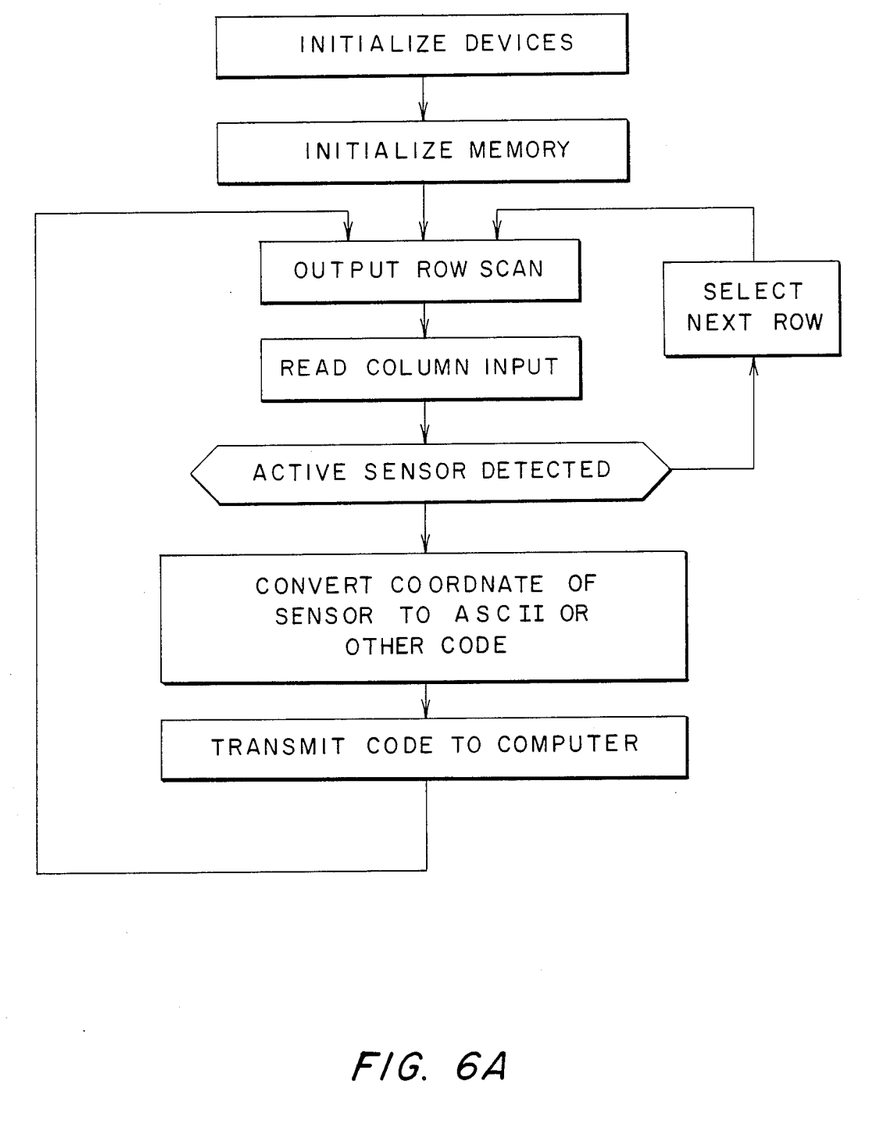
FIG. 6A is a flow chart of the programmable steps performed in processing the input entered at the keyboard to data supplied to the computer.

Now referring to FIGS. 5 and 6 there is illustrated further apparatus for interfacing the data from the keyboard 16 for both serial and parallel bidirectional input to a computer 217. FIG. 5 illustrates an encoder 220 which connects the amplifier output conductors 176-190 to a socket connection 222. FIG. 6 illustrates an interface board generally designated by the numeral 218.

The encoder 220 is connected to the outputs of the amplifiers 160-174 and is connected through conductors 226, 228, and 230 and socket connection 222 to the input terminal 124 which is also shown in FIG. 4. The interface board 218, shown in FIG. 6, is connected between the photosensor matrix 50 and the data output connectors 176-190, shown in FIG. 5. When the interface board 218 is utilized, all scanning and reading of the array 50 of photosensors 22 are performed by the interface board 218. In this respect the interface board 218 serves an output conditioner for converting the amplifier outputs to a form readable by the computer 14.

The output from the interface board 218 is also capable of being controlled by the computer 217, shown in FIG. 6, which scans the keyboard 16 to provide a binary count of the row on the keyboard 16 being scanned. This binary count is impressed on three conductors A, B, and C of the input terminal 124, shown in FIG. 4, to the demultiplexer 120. In this manner the computer 217 scans the keyboard 16 and formats the data.

When an actuated sensor 22 is detected by the scanning operation performed by the demultiplexer 120 shown in FIG. 4, the X-Y coordinate of the actuated sensor 22 is identified as a preselected signal, such as a standard ASCII signal. The output from the optical keyboard 16 is transmitted through the parallel connection of the selector amplifier board 118 (FIG. 4) to the board 218 (FIG. 6) and the encoder 220 (FIG. 5). The interface board 218 converts the data received from the amplifier board 118 to output in a format read by the computer. With this arrangement the computer does not have to be programmed specifically for the optical keyboard 16.

The selector amplifier board 118 (FIG. 4) is serially connected to the encoder 220 (FIG. 5) by socket 222 through the input terminal 124. Thus the encoder 220 is connected through the input terminal 124 of the amplifier board 118 shown in FIG. 4. The input terminal 124 includes the three conductors A, B and C. With this arrangement the optical keyboard 16 is adapted for connection to computers that utilize a standard parallel or serial data format.

Figure 7:
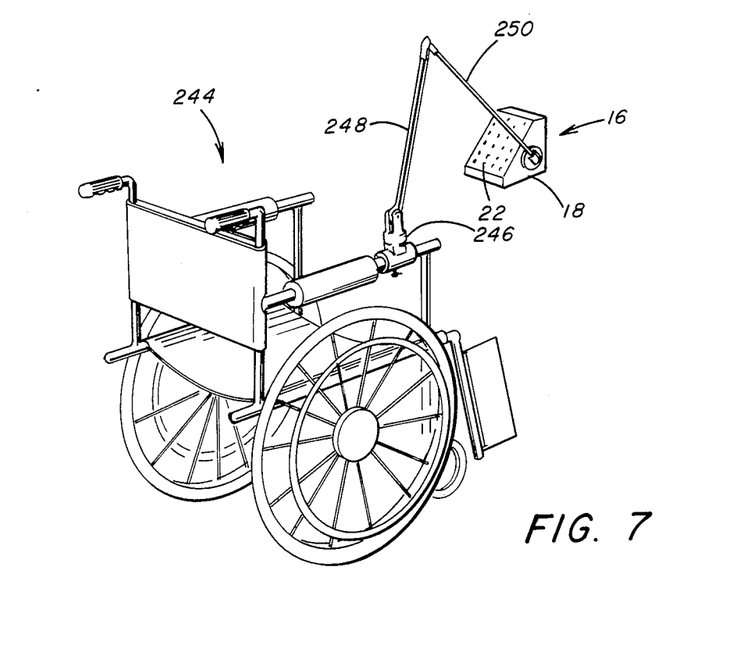
FIG. 7 is a schematic illustration of a wheelchair, illustrating an arrangement for mounting the optical keyboard of the present invention in a position accessible for use by a handicapped person sitting in the wheelchair.

A crystal display can also be used with the keyboard 16. A crystal display receives data from the computer for instructions to be read by the operator. Use of a crystal display also permits the operator to read the data transmitted from the optical keyboard 16. The socket 222 is connected by conductors 226, 228, and 230 to the encoder 220. The socket 222 also includes additional terminals 232-242 for connection to additional apparatus for remote control by the optical keyboard 16, for example, remote control of a wheelchair 224 as shown in FIG. 7, which will be described later in greater detail.

As discussed above upon activation of a sensor 22 a strobe signal in a three bit binary code is generated. The strobe signal is generated by the encoder 220 (FIG. 5) and transmitted through conductor 235 to the socket connection 222 connected to the computer 217 (FIG. 6). The strobe signal indicates a column where the light beam was detected. Thus the scanning operation detects the presence of a strobe signal.

The socket 222, also shown in FIG. 6, is connected to receive input from the plug 52 of the array of sensors 22 through the demultiplexer 120 (FIG. 4) and the socket 222. A bidirectional data path is provided between the socket 222 and a microcomputer 237, shown in FIG. 6. The microcomputer 237 converts the data from the keyboard 16 to either a serial or parallel interface format.

An interface connector 239 converts the data to a format for serial input to the computer 217. A second interface connector 241 provides for a parallel input of the data to the computer 217. Also the connection between the microcomputer 237 and the computer 217 is bidirectional through the connectors 239 and 241.

The computer 217 is operable to transmit data back through the microcomputer 237 to the keyboard 16 for display on a monitor 243. In this manner any data transmitted from or to the keyboard 16 is displayed on the monitor 243. Thus a handicapped operator is capable of communicating with the computer 217.

The computer 217 through the interface board 218 is operable as a means of personal communication for the handicapped operator. The data transmitted by actuation of the sensors 22 is not confined to keyboard characters expressed in terms of a X-Y coordinate. Data can also be expressed in entire strings of characters for sending a message. The interface board 218 can be programmed to transmit data in this format also.

As illustrated in FIG. 7, the wheelchair 244 is conventional in design and is adapted to support the optical keyboard 16 for use by a handicapped operator who is confined to the wheelchair to the extent that the individual has little or no use of his arms or legs. The optical keyboard 16 is supported in a manner to facilitate actuation of the photosensors 22 by casting a beam of light from a light source. As illustrated in FIG. 1, the light source 26 can be mounted on a headband 28. With the operator having control of head movement, selected sensors 22 in the array on the keyboard 62 are actuated in a sequence selected by the operator. By moving the head the light beam 24 is cast for a preselected period of time upon a specific sensor 22.

The keyboard housing 18 can be supported in a number of ways on the wheelchair and an exemplary arrangement is illustrated in FIG. 7. A swivel support 246 is securely attached to one of the arms of the wheelchair 244. A first support rod 248 is mounted on the support 246 to permit the rod 248 to swivel on the support 246. The upper end of the support rod 248 is pivotally connected to one end of an arm 250. The opposite end of the arm 250 is connected to the keyboard housing 18 in a manner to permit movement of the housing 18 for adjusting the position of the keyboard 16 into and out of an operative position for use by the handicapped operator.

Movement of the support rod 248 about the support 246 moves the keyboard 16 toward and away from the operator. The elevation of the keyboard 16 can be adjusted by pivoting the arm 250 relative to the rod 248. Final elevational and tilting adjustments are made by moving the keyboard housing 18 about its connection to the end of the arm 250.

With the keyboard 16 adjustably mounted on the wheelchair 244, the wheelchair operator by selected head movements casts a light beam 24 to actuate the photosensors 22 in a selected sequence. Accordingly, with the keyboard 16 electrically connected through the interface apparatus 10 as above described to a computer 14, the otherwise incapacitated operator can perform many tasks not otherwise available to the individual. Also, by linking the computer 14 to other devices, a handicapped operator can perform a number of work related tasks, such as, control of a robot in a manufacturing operation.

Figure 8:
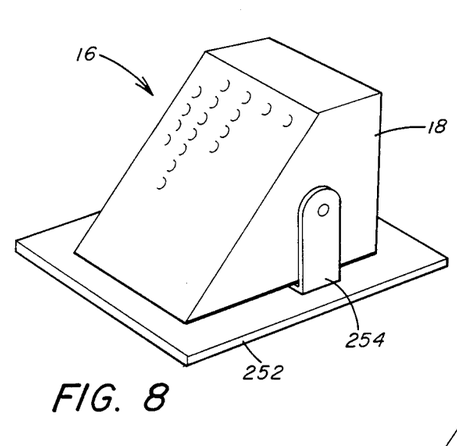
FIG. 8 is a schematic illustration of apparatus for mounting the optical keyboard for tilting movement on a wheelchair or other device for use by a handicapped person.
Figure 9:
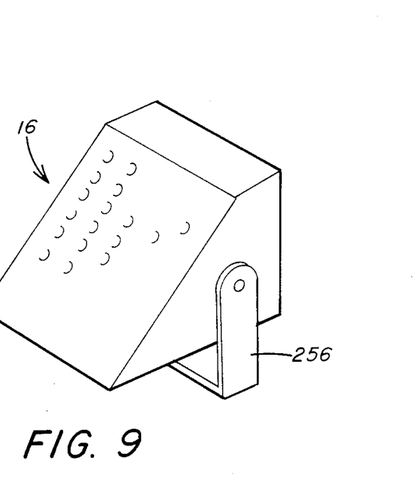
FIG. 9 is a schematic illustration similar to FIG. 6, illustrating another embodiment for mounting the optical keyboard of the present invention.

FIGS. 8 and 9 schematically illustrate other arrangements by which the keyboard 22 can be mounted for selectively positioning the keyboard 22. As illustrated in FIG. 8 the keyboard 16 is mounted on a base 252, which is secured to the arm of a wheelchair. In this manner the base 252 is movable about a vertical axis. A U-shaped bracket 254 is secured to the base 252. The housing 18 of the keyboard 16 is pivotally secured to the upper ends of the arms of the bracket 254 for tilting or pivotal movement of the housing 18 about horizontal axis.

FIG. 9 illustrates a similar arrangement in which the keyboard 16 is mounted on a tilt bracket 256 which can be rigidly secured, for example, to the arm of a wheelchair. With this arrangement the keyboard 16 is pivotal about a horizontal axis through the upper ends of the arms of the tilt bracket 256. It should be understood that the arrangements illustrated in FIGS. 7–9 are only representative of a wide variety of arrangements by which the optical keyboard 16 can be positioned to a support means to facilitate its operation by a handicapped operator who has little or not movement of the body except for movement of the head.

According to the provisions of the patent statutes, I have explained the principle, preferred construction and mode of operation of my invention, and have illustrated and described what I now consider to represent its best embodiments. However, it should be understood that within the scope of the appended claims, the invention may be practiced otherwise than as specifically illustrated and described.

I claim:

1. Interface apparatus for a data processor comprising,
    a data entry terminal including an array of photosensors,
    a monitor for visually displaying data, said monitor associated with said data entry terminal,
    said photosensors being positioned in a X-Y coordinate system having a plurality of rows of photosensors parallel with a X-axis and a plurality of columns of photosensors parallel with a Y-axis for identifying each photosensor by a X and Y coordinate,
    said photosensors being actuated or not actuated between an active state and an inactive state in dependence upon receipt of energy from a source of energy to generate input signals,
    a microprocessor board having a data input terminal,
    data input lines electrically connecting said data input terminal in a first network to all of said sensors in said X-axis and in a second network to all of said photosensors in said Y-axis,
    said data input terminal on said microprocessor board receiving input signals from said photosensors upon receipt of energy representing a selected X and Y coordinate in said array of photosensors,
    data processing means for receiving output signals from said microprocessor board in response to said input signals from said actuated sensors as instructions to perform a task,
    means associated with said data processing means for transmitting data commands through said microprocessor board for display on said monitor,
    bidirectional data means connecting said data entry terminal, said microprocessor board, and said data processing means for simultaneous transfer of data between said data entry terminal and said data processing means,
    means on said microprocessor board for sensing said input signals from said array of photosensors sequentially row by row parallel to said X-axis to identify said photosensors aligned with said Y-axis being actuated,
    said microprocessor board including an output terminal connected to said data processing means for transmitting said output signals representing each actuated photosensor by X and Y coordinates to said data processing means, and
    said data processing means in response to said output signals from said microprocessor board being operable to perform said task in response to actuation of said photosensors when exposed to a source of energy.

2. Interface apparatus as set forth in claim 1 which includes,
    means for generating a signal indicating actuation of said photosensors when exposed to a source of energy to generate said input signals.

3. Interface apparatus as set forth in claim 2 which includes,
    a visible signal corresponding to each of said photosensors upon actuation thereof.

4. Interface apparatus as set forth in claim 2 which includes,
    an audio signal corresponding to each of said photosensors upon actuation thereof.

5. Interface apparatus as set forth in claim 1 in which,
    said means for sensing said input signals from said array of photosensors includes a scanning circuit,
    said scanning circuit being connected through said microprocessor board to said data processing means, and
    said scanning circuit being operable to identify the activated photosensor by a X and Y coordinate.

6. Interface apparatus as set forth in claim 1 which includes,
    a parallel interface connecting said microprocessor board output terminal to said data processing means, and
    means for receiving said output signals from said microprocessor board to generate a corresponding signal for transmission through said parallel interface to said processing means.

7. Interface apparatus as set forth in claim 1 which includes,
    a serial interface connecting said microprocessor board output terminal to said data processing means, and
    means for receiving said output signals from said microprocessor board to generate a corresponding signal for transmission through said serial interface to said processing means.

8. An optical computer interface comprising,
    an array of light sensitive elements positioned in a coordinate system,
    said elements each being individually actuated when exposed to a light source to transmit a signal,
    comparator means for comparing said signal transmitted by each of said actuated elements with a reference signal and generating an output signal corresponding to said actuated element,
    scanning means for sequentially inspecting said array of elements to identify which one of said elements is being actuated and provide a coordinate for each actuated element, said coordinate being expressed in terms of an output signal, an encoder for receiving said output signal, and said encoder converting said output signal representing a coordinate from said scanning means to data in a format adaptable for entry to a computer for data processing.

9. An optical computer interface as set forth in claim 8 in which, said elements are positioned in a X-Y coordinate system, and said elements being positioned in a plurality of rows forming X-axes and in a plurality of columns forming Y-axes.

10. An optical computer interface as set forth in claim 9 in which, said scanning means scans said rows of elements to identify the columns containing an actuated element, and comprising an encoder for receiving from said scanning means data expressed in terms of the X-Y coordinates.

11. An optical computer interface as set forth in claim 10 in which, said comparator means includes a plurality of amplifiers for receiving signals corresponding to the column position of the row containing an actuated element, each of said amplifiers having an input and an output terminal representing a column position in the X-Y coordinate system of said elements, said amplifiers supplying output signals upon actuation of an element in a respective one of said rows, an encoder connected to receive said output signals from said amplifiers, a computer connected to receive input from said encoder, and said encoder being operable to convert said output signals from said amplifier to said input readable by said computer.

12. A method for the optical entry of information for data processing comprising the steps of, selectively actuating one of a plurality of photosensors in an array of photosensors, identifying the position of each photosensor in the array when actuated by a selected coordinate, transmitting from the photosensor upon actuation an output signal, said output signal generated from the array and corresponding to the coordinate of the actuated photosensor, scanning the array of photosensors to identify the location of an actuated photosensor, associating a set of coordinates with each actuated photosensor to identify the position of the output signals from the array of photosensors, and converting the identified output signals to data input signals having a format representative of information for input to data processing means.

13. A method for the optical entry of information as set forth in claim 12 which includes, converting the output signal from the actuated photosensor after scanning the array of photosensors to a data input signal for transmission through a serial connection to data processing means.

14. A method for the optical entry of information as set forth in claim 12 which includes, converting the output signal from the actuated photosensor after scanning the array of photosensors to a data input signal for transmission through a parallel connection to data processing means.

15. A method for the optical entry of information as set forth in claim 12 which includes, displaying data representing the output signals transmitted from the array of photosensors, generating from the data processing means signals responsive to the output signals from the actuated photosensors, and displaying data representing the signals from the data processing means.

* * * * *